(12) United States Patent
Srinivasan et al.

(10) Patent No.: US 11,406,431 B1
(45) Date of Patent: Aug. 9, 2022

(54) SYSTEMS AND METHODS OF USE AND MODULAR INSTRUMENTS WITH A LATERAL REDUCER

(71) Applicant: Warsaw Orthopedic, Inc., Warsaw, IN (US)

(72) Inventors: Vignesh Srinivasan, Chennai (IN); Thomas J. Stinchfield, Germantown, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 17/315,782

(22) Filed: May 10, 2021

(51) Int. Cl.
*A61B 17/70* (2006.01)
*A61B 17/00* (2006.01)

(52) U.S. Cl.
CPC ............ *A61B 17/7086* (2013.01); *A61B 2017/00407* (2013.01)

(58) Field of Classification Search
CPC ............ A61B 17/7083; A61B 17/7085; A61B 17/7086; A61B 17/7088; A61B 2017/00407
USPC .......................................... 606/86 A, 99, 104
See application file for complete search history.

(56) References Cited

U.S. PATENT DOCUMENTS

| | | |
|---|---|---|
| 7,618,424 B2 | 11/2009 | Wilcox et al. |
| 7,794,464 B2 | 9/2010 | Bridwell et al. |
| 7,811,288 B2 * | 10/2010 | Jones ............... A61B 17/7011 606/279 |
| 8,147,524 B2 | 4/2012 | Piza Vallespir |
| 8,162,952 B2 | 4/2012 | Cohen et al. |
| 8,192,440 B2 | 6/2012 | Jones et al. |
| 8,211,110 B1 | 7/2012 | Corin et al. |
| 8,221,474 B2 | 7/2012 | Bridwell et al. |
| 8,277,453 B2 | 10/2012 | Kave et al. |
| 8,394,109 B2 | 3/2013 | Hutton et al. |
| 8,475,467 B2 | 7/2013 | Manninen |
| 8,491,590 B2 | 7/2013 | Stad et al. |
| 8,500,741 B2 | 8/2013 | Hansen |
| 8,608,746 B2 | 12/2013 | Kolb et al. |

(Continued)

OTHER PUBLICATIONS

CD Horizon Solera 5.5/6.0mm Spinal System with SMARTLINK Extender and Derotator Instruments, Metronic Sofamor Danet USA, Inc. © 2013.

(Continued)

*Primary Examiner* — Eduardo C Robert
*Assistant Examiner* — Christina Negrellirodriguez
(74) *Attorney, Agent, or Firm* — Fox Rothschild LLP

(57) ABSTRACT

A lateral reducer includes a translating reducer arm, an interface and handle bars. The arm includes a first longitudinal axis and laterally drives a rod. The interface has a fulcrum and a first side integrated with the arm. The interface pivots the arm between an open position and a closed position. A first handle bar connects to the fulcrum and has a second longitudinal axis. A second handle bar connects to a second side of the interface. The second handle bar has a first position, intermediate positions and a second position. In the first position, the arm is in the open position. In the second position, the arm is in the closed position so that the first longitudinal axis and the second longitudinal axis are parallel. In intermediate positions between the first and second positions, the arm moves laterally in a direction toward the first handle bar.

20 Claims, 10 Drawing Sheets

(56) References Cited

U.S. PATENT DOCUMENTS

| | | |
|---|---|---|
| 8,608,782 B1 | 12/2013 | Rovner |
| 8,623,022 B2 | 1/2014 | Forton et al. |
| 8,636,743 B2 | 1/2014 | Jones et al. |
| 8,672,944 B2 | 3/2014 | Boachie-Adjei et al. |
| 8,702,713 B2 | 4/2014 | Nayet et al. |
| 8,821,502 B2 | 9/2014 | Gleeson et al. |
| 8,894,655 B2 | 11/2014 | Fallin et al. |
| 8,900,248 B2 | 12/2014 | Biyani |
| 8,906,034 B2 | 12/2014 | Gleeson et al. |
| 8,951,257 B2 | 2/2015 | Lenke et al. |
| 8,956,360 B2 | 2/2015 | Boachie-Adjei et al. |
| 8,979,851 B2 | 3/2015 | Fallin et al. |
| 9,005,204 B2 | 4/2015 | Manninen et al. |
| 9,011,447 B2 | 4/2015 | Arnett et al. |
| 9,060,825 B2 | 6/2015 | Hutton et al. |
| 9,066,762 B2 | 6/2015 | Jones et al. |
| 9,101,412 B2 | 8/2015 | Bootwala et al. |
| 9,119,684 B2 | 9/2015 | Fallin et al. |
| 9,131,967 B2 | 9/2015 | Stad et al. |
| 9,155,573 B2 | 10/2015 | May et al. |
| 9,179,957 B2 | 11/2015 | Ibrahim et al. |
| 9,198,692 B1 | 12/2015 | Doose et al. |
| 9,241,742 B2 | 1/2016 | Stad |
| 9,247,977 B2 | 2/2016 | Fallin et al. |
| 9,254,152 B2 | 2/2016 | Manninen |
| 9,259,245 B2 | 2/2016 | Maruenda Paulino et al. |
| 9,289,248 B2 | 3/2016 | Seex et al. |
| 9,289,251 B2 | 3/2016 | Leroux et al. |
| 9,308,030 B2 | 4/2016 | Manninen |
| 9,314,273 B2 | 4/2016 | Iott et al. |
| 9,314,280 B2 | 4/2016 | Corin |
| 9,326,798 B2 | 5/2016 | Kolb et al. |
| 9,402,660 B2 | 8/2016 | Brinkman et al. |
| 9,414,860 B2 | 8/2016 | Boachie-Adjei et al. |
| 9,468,476 B2 | 10/2016 | Boachie-Adjei et al. |
| 9,480,500 B2 | 11/2016 | Ibrahim et al. |
| 9,480,504 B1 | 11/2016 | Schafer et al. |
| 9,561,062 B2 | 2/2017 | Hayes et al. |
| 9,579,140 B2 | 2/2017 | Jones et al. |
| 9,655,685 B2 | 5/2017 | Fallin et al. |
| 9,668,776 B2 | 6/2017 | Ibrahim et al. |
| 9,681,899 B2 | 6/2017 | Artaki et al. |
| 9,693,806 B2 | 7/2017 | Manninen et al. |
| 9,808,295 B2 | 11/2017 | Peukert et al. |
| 9,861,393 B2 | 1/2018 | Ibrahim et al. |
| 9,877,750 B2 | 1/2018 | Iott et al. |
| 9,888,945 B2 | 2/2018 | Walters et al. |
| 9,907,582 B1 | 3/2018 | Olea |
| 9,974,577 B1 | 5/2018 | Smith et al. |
| 10,028,771 B2 | 7/2018 | Artaki et al. |
| 10,028,773 B2 | 7/2018 | Ibrahim et al. |
| 10,028,774 B2 | 7/2018 | Meyer |
| 10,034,695 B1 | 7/2018 | Schafer et al. |
| 10,070,900 B2 | 9/2018 | Hayes et al. |
| 10,070,936 B2 | 9/2018 | Fallin et al. |
| 10,085,807 B2 | 10/2018 | Butters et al. |
| 10,098,665 B2 | 10/2018 | Rutschmann et al. |
| 10,111,650 B2 | 10/2018 | Nel |
| 10,213,232 B2 | 2/2019 | Ibrahim et al. |
| 10,390,862 B2 | 8/2019 | Bobbitt et al. |
| 10,426,538 B2 | 10/2019 | Jones et al. |
| 10,617,449 B2 | 4/2020 | Corbin et al. |
| 10,682,166 B2 | 6/2020 | Smith et al. |
| 10,687,867 B2 | 6/2020 | Artaki et al. |
| 10,687,868 B2 | 6/2020 | Heuer |
| 10,709,477 B2 | 7/2020 | Manninen et al. |
| 10,716,600 B1 | 7/2020 | Olea et al. |
| 10,716,601 B2 | 7/2020 | Schafer et al. |
| 10,765,488 B2 | 9/2020 | Fallin et al. |
| 10,772,662 B2 | 9/2020 | Rezach |
| 2005/0021040 A1 | 1/2005 | Bertagnoli |
| 2008/0077155 A1 | 3/2008 | Diederich et al. |
| 2008/0172062 A1 | 7/2008 | Donahue et al. |
| 2012/0203279 A1 | 8/2012 | Walters et al. |
| 2014/0107707 A1 | 4/2014 | Rovner |
| 2015/0335359 A1 | 11/2015 | May et al. |
| 2017/0020583 A1 | 1/2017 | Tsai et al. |
| 2018/0185169 A1 | 7/2018 | Kurtaliaj et al. |
| 2019/0090908 A1 | 3/2019 | Stad |
| 2019/0142475 A1 | 5/2019 | Ibrahim et al. |
| 2019/0231394 A1 | 8/2019 | Bechtel et al. |
| 2020/0054361 A1 | 2/2020 | Peultier et al. |
| 2020/0107862 A1 | 4/2020 | Biedermann et al. |
| 2020/0179008 A1 | 6/2020 | Biedermann et al. |
| 2020/0237410 A1 | 7/2020 | Gabos et al. |
| 2020/0297393 A1 | 9/2020 | Olea et al. |
| 2020/0297394 A1 | 9/2020 | Schafer et al. |
| 2020/0305932 A1 | 10/2020 | Park |

OTHER PUBLICATIONS

CD Horizon Solera 5.5/6.0 Spinal Syste Surgical Technique, Medtronic Sofamor Danek, © 2014.

* cited by examiner

__US 11,406,431 B1__

SYSTEMS AND METHODS OF USE AND MODULAR INSTRUMENTS WITH A LATERAL REDUCER

FIELD

The present technology is generally related systems and methods of use and surgical instruments such as lateral reducers and extenders and/or derotators that secure spinal constructs including bone fasteners and connectors for treating the spine.

BACKGROUND

Spinal disorders of the spine may result in symptoms, such as without limitation, nerve damage, and partial or complete loss of mobility and chronic pain. Surgical treatment of these spinal disorders includes correction, fusion, fixation, discectomy, laminectomy and implantable prosthetics, for example. As part of these surgical treatments, vertebral rods and bone fasteners are often used to provide stability to a treated region. During surgical treatment, a surgeon uses various surgical instruments, such as extenders, reducers and derotators, to implant one or more rods and bone fasteners to a surgical site. Extenders, for example, are used with reducers to implant a rod.

During surgery, in certain situations, the rod rests medially or laterally relative to the top of the implant, such as a head of a bone fastener. However, the rod needs to be align with the implant. In some situations, the rod is long with multiple instruments already installed around the rod. Thus, aligning the rod that is medially or laterally offset from the implant can be a challenge especially when the surgical site is crowded with other instruments.

This disclosure describes an improvement over these prior art technologies.

SUMMARY

The techniques of this disclosure generally relate to a system with a modular surgical instrument that includes an extender and a lateral reducer to, for example, sequentially reduce a rod laterally. The lateral reducer may remain installed on the extender as the rod is further reduced into the implant head, during implantation of the fastener and/or during derotation.

In one aspect, the present disclosure provides a lateral reducer that may include a translating reducer arm including a first longitudinal axis and configured to laterally drive a rod. The lateral reducer may include a pivoting arm interface having a fulcrum and a first side integrated with the reducer arm. The pivoting arm interface pivots the reducer arm about the fulcrum between an open position and a closed position. The lateral reducer may include a first handle bar coupled to the pivoting arm interface at the fulcrum and has a second longitudinal axis. The lateral reducer may include a second handle bar coupled to a second side of the pivoting arm interface. The second handle bar may be moveable between a first position, intermediate positions and a second position. In the first position, the reducer arm is in the open position. In the second position, the reducer arm is in the closed position such that the first longitudinal axis and the second longitudinal axis are parallel. In intermediate positions between the first position and the second position, the reducer arm moves laterally in a direction toward the first handle bar.

Another aspect of the disclosure provides a modular surgical instrument that includes an extender including a modular instrument interface, an extender leg having a first longitudinal axis and a head cavity portion at an end of the extender leg. The instrument may include a lateral reducer. The lateral reducer includes a translating reducer arm including a second longitudinal axis. The reducer arm may have an open position orienting the second longitudinal axis angled relative to the first longitudinal axis and a closed position orienting the second longitudinal axis aligned with the first longitudinal axis. The lateral reducer may include a first handle bar coupled to modular instrument interface and a second handle bar coupled to the translating reducer arm. The second handle bar sequentially pivots the reducer arm laterally toward the extender leg to the closed position.

In another aspect, the disclosure provides a method that may include providing the modular surgical instrument having an extender and lateral reducer. The method may include coupling a first handle bar of a lateral reducer to a modular instrument interface of an extender; by the lateral reducer, sequentially reducing laterally a rod toward a leg of the extender; and prior to laterally reducing the rod, locking a head of a bone fastener in the extender.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
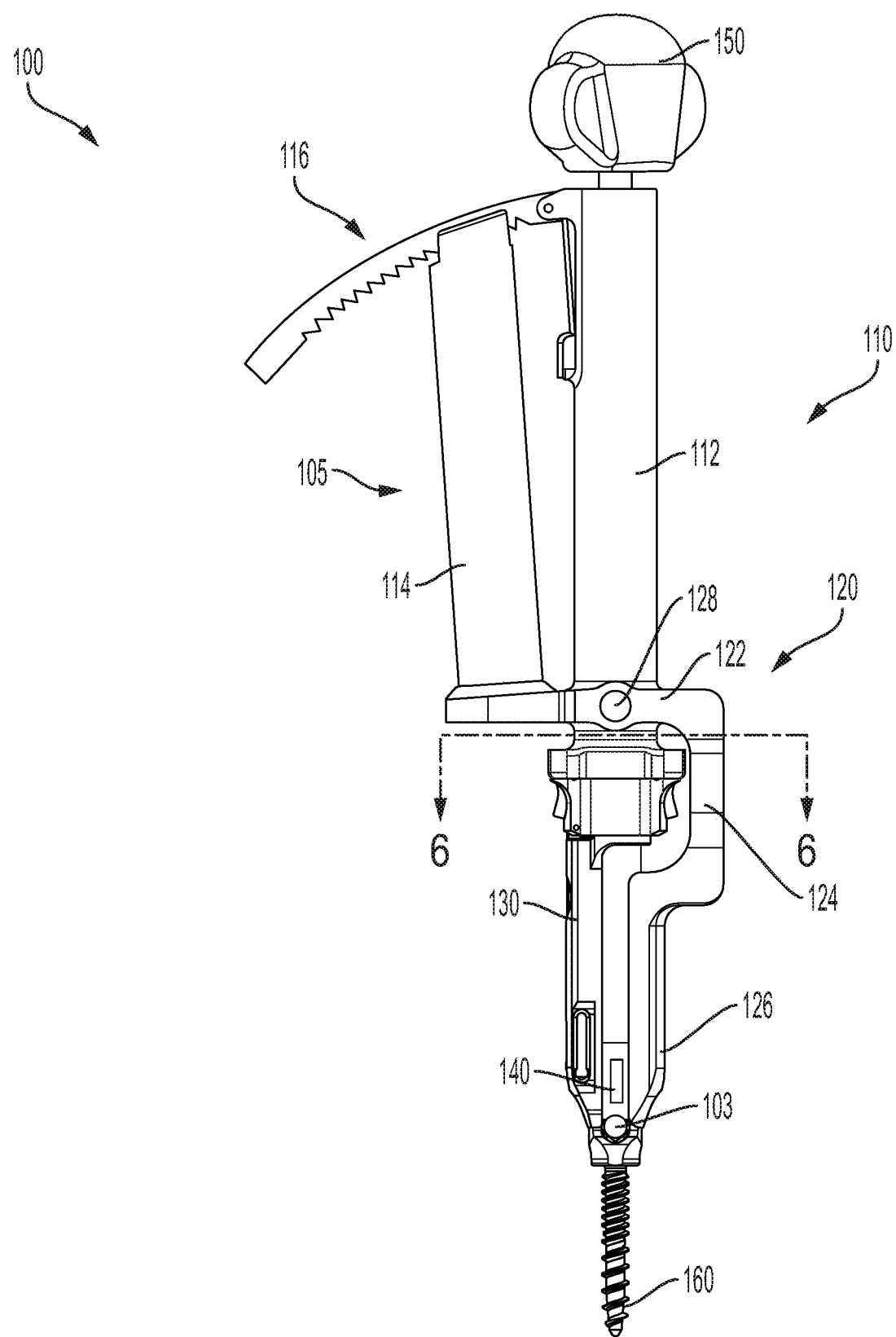
FIG. 1 is a side view that illustrates components of a modular surgical implant system for the treatment of a patient's spine.

The embodiments of the modular surgical implant system are discussed in terms of medical devices for the treatment of musculoskeletal disorders and more particularly, in terms of a surgical system and a method for treating a spine. In the embodiments, the system may include a modular surgical instrument that may include an extender and a lateral reducer having handle bars configured to be mounted to the open extender and a translating reducer arm, for example, to laterally drive a rod toward the extender, and the related methods of use that can be employed with spinal constructs including bone fasteners and connectors that provide a surgical implant system for spine surgeons.

The embodiments of the modular surgical implant system may be used for posterior, non-cervical fixation as an adjunct to fusion for the following indications: degenerative disc disease (defined as back pain of discogenic origin with degeneration of the disc confirmed by history and radiographic studies), spondylolisthesis, trauma (i.e., fracture or dislocation), spinal stenosis, curvatures (i.e., scoliosis, kyphosis, or lordosis), tumor, pseudarthrosis, and/or failed previous fusion.

The system of the present disclosure may be understood more readily by reference to the following detailed description of the embodiments taken in connection with the accompanying drawing figures that form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, front, back, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of and/or reducing the likelihood of a certain disease or undesirable condition (e.g., preventing or reducing the likelihood of the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical implant system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIG. 1, components of a surgical implant system 100 are illustrated, in accordance with the principles of the disclosure.

The components of system 100 can be fabricated from biologically acceptable materials suitable for medical applications, including metals, synthetic polymers, ceramics and bone material and/or their composites. For example, the components of system 100, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologic Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of system 100 may have material composites, including the above materials, to achieve various desired characteristics such as strength, rigidity, elasticity, compliance, biomechanical performance, durability and radiolucency or imaging preference. The components of system 100, individually or collectively, may also be fabricated from a heterogeneous material such as a combination of two or more of the above-described materials. The components of system 100 may be monolithically formed, integrally connected or include fastening elements and/or instruments, as described herein.

The system 100 may include at least one modular surgical instrument 105 (FIG. 2) and be employed, for example, with an open or mini-open, minimal access and/or minimally invasive including percutaneous surgical technique to deliver and fasten an implant at a surgical site within a body of a patient, for example, a section of a spine. In one embodiment, the components of system 100 may be configured to implant and/or fix a bone fastener, such as a pedicle screw, or other implants within tissue for a surgical treatment to treat various spine pathologies, such as those described herein.

Figure 2:
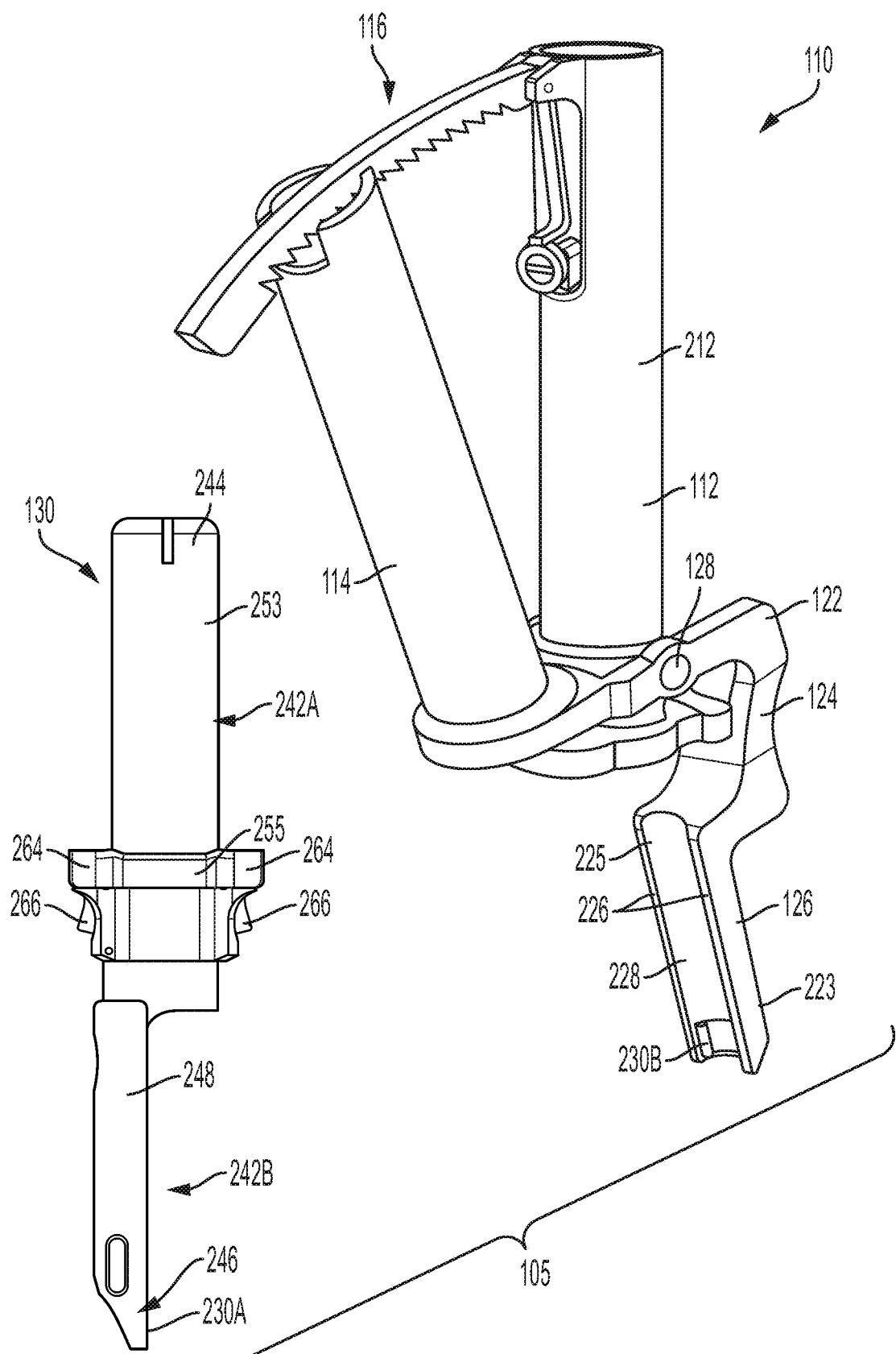
FIG. 2 is a diagram of a perspective view that illustrates components of a modular surgical instrument.

FIG. 1 is a side view that illustrates components of the modular surgical implant system 100. FIG. 2 is a diagram of a perspective view that illustrates a modular surgical instrument 105. A surgeon when performing surgical deformity procedures may need to manipulate the spine and reduce the spinal curvature using an elongated rod 103 to be put in place using a modular surgical instrument 105 such as, without limitation, using a lateral reducer 110 and open extender 130. The system 100 may include a vertical rod pusher 140 (FIG. 4), other tools, such as driver 150 (FIG. 5), and fasteners 160, such as described in "CD Horizon® Solera® 5.5/6.0 Spinal System," by Medtronic, Inc., copyright date 2014, which is incorporated herein by reference in its entirety. Example, open extenders are also described in U.S. patent application Ser. No. 17/169,920, titled "SYSTEMS, METHODS OF USE AND SURGICAL INSTRUMENTS EMPLOYING A SECURE SLIDE LOCK TO FASTEN A HEAD," incorporated herein by reference in its entirety.

Figure 6:
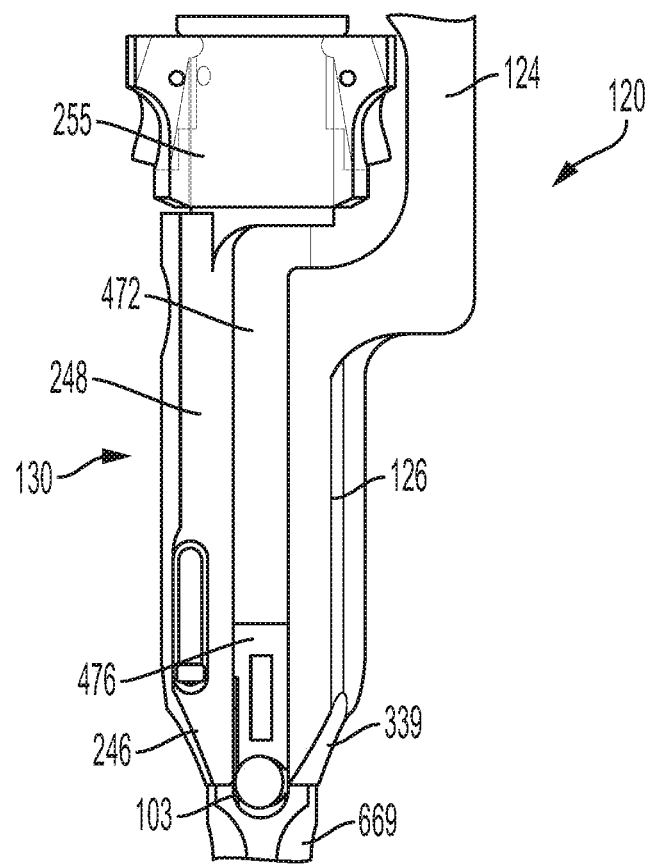
FIG. 6 is a sectional view below plane 6-6 of FIG. 1 that illustrates components of the modular surgical instrument system.
Figure 7A:
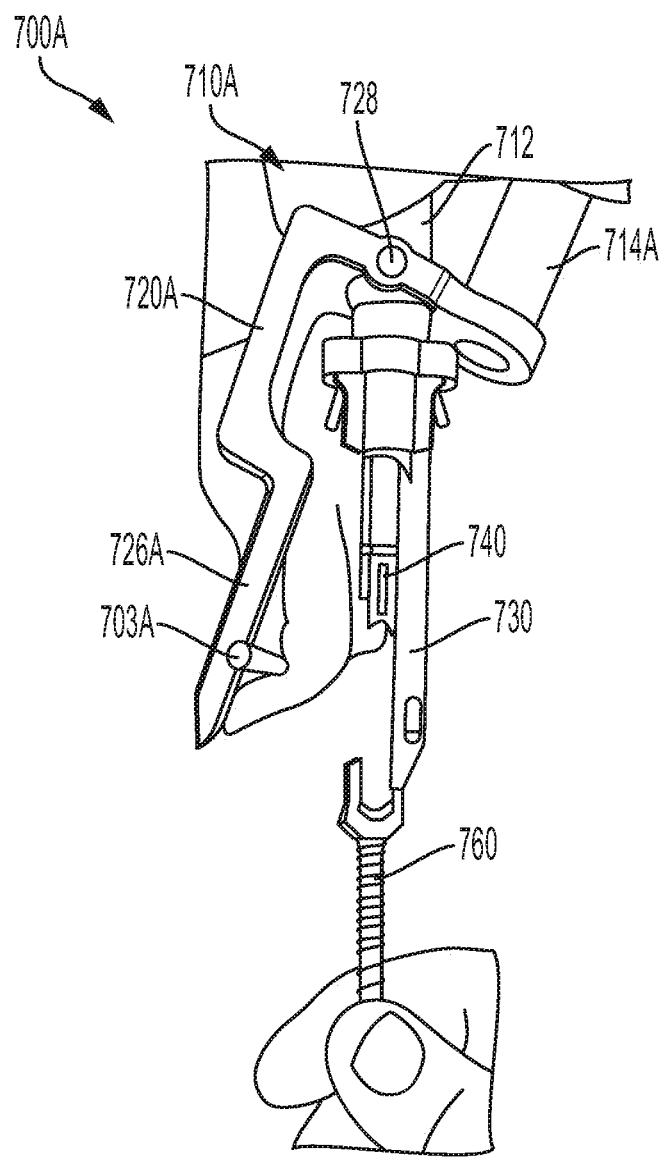
FIG. 7A is a partial side view that illustrates the modular surgical implant system of FIG. 1 in a first (open) orientation.
Figure 7B:
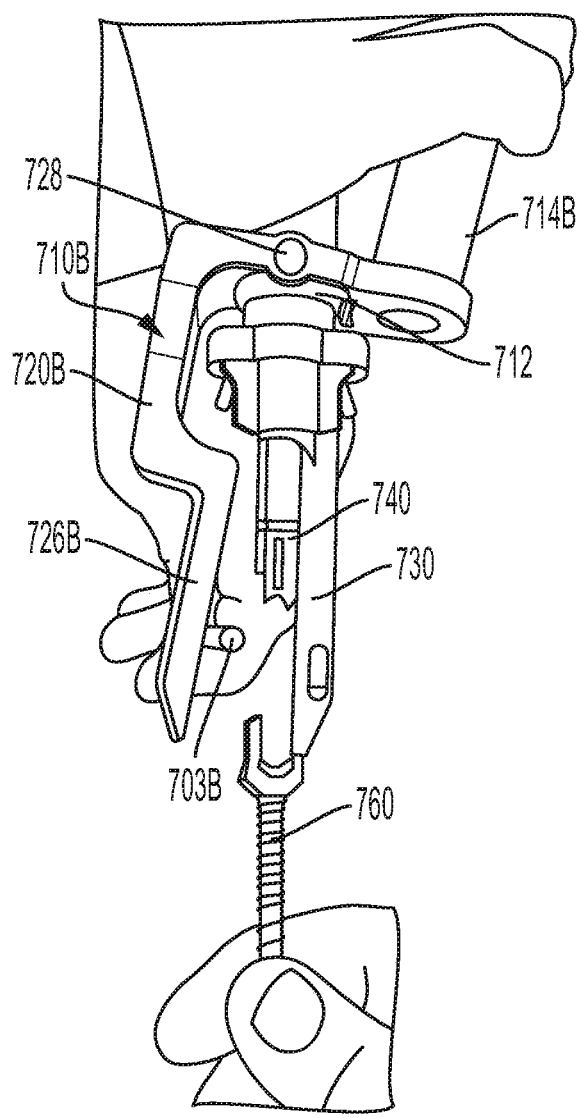
FIG. 7B is a partial side view that illustrates the modular surgical implant system of FIG. 1 in an intermediate orientation.
Figure 7C:
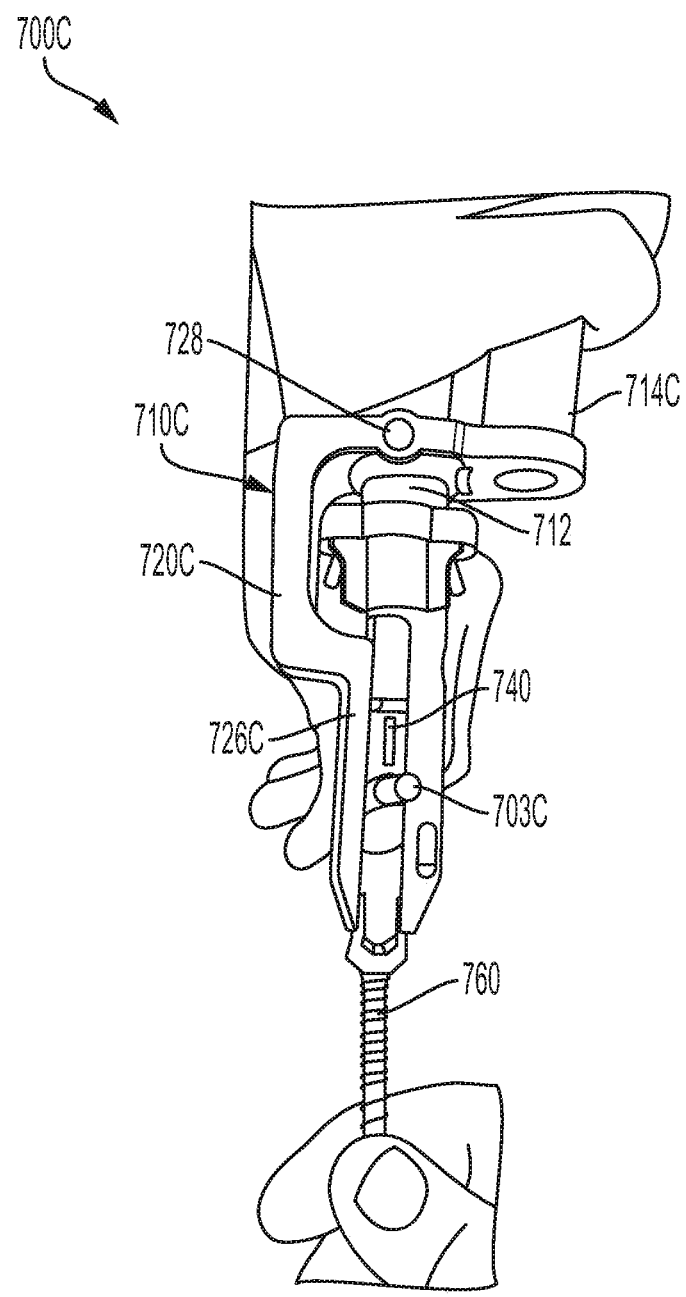
FIG. 7C is a partial side view that illustrates the modular surgical implant system of FIG. 1 in a second (closed) orientation.

The lateral reducer 110 may include handle bars 112 and 114. The lateral reducer 110 may include a ratchet assembly 116 linking together the handle bars 112 and 114. The lateral reducer 110 may include a pivoting arm interface 120 having a fulcrum 128 and a first side integrated with the translating reducer arm 126. The term "integrated" may include combining, joining, connecting, coupling or attaching the pivoting arm interface 120 to the translating reducer arm 126 to form a unitary structure or multi-part structure. In some embodiments, the integration may use a fastener such as glue, adhesive, friction fit connections, screws, pins, welding material or the like. The pivoting arm interface 120 may be a seesaw interface that may pivot about fulcrum 128. As the interface 120 pivots, the reducer arm 126 laterally rotates between an open position, as seen in FIG. 7A, and a closed position, as seen in FIGS. 1, 6 and 7C.

The pivoting arm interface 120 may include a bracket, which may have a first bracket member 122 and a second bracket member 124. The first bracket member 122 may have a longitudinal axis angled relative to the first longitudinal axis LA1 (FIG. 2) of handle bar 112. The second bracket member 124 may be integrated with the first bracket member 122. The second bracket member 124 may having an L-shape to from a C-shaped translation offset with the first bracket member 122. The reducer arm 126 may be integrated with and depend from a free end of the C-shaped translation offset.

Figure 4:
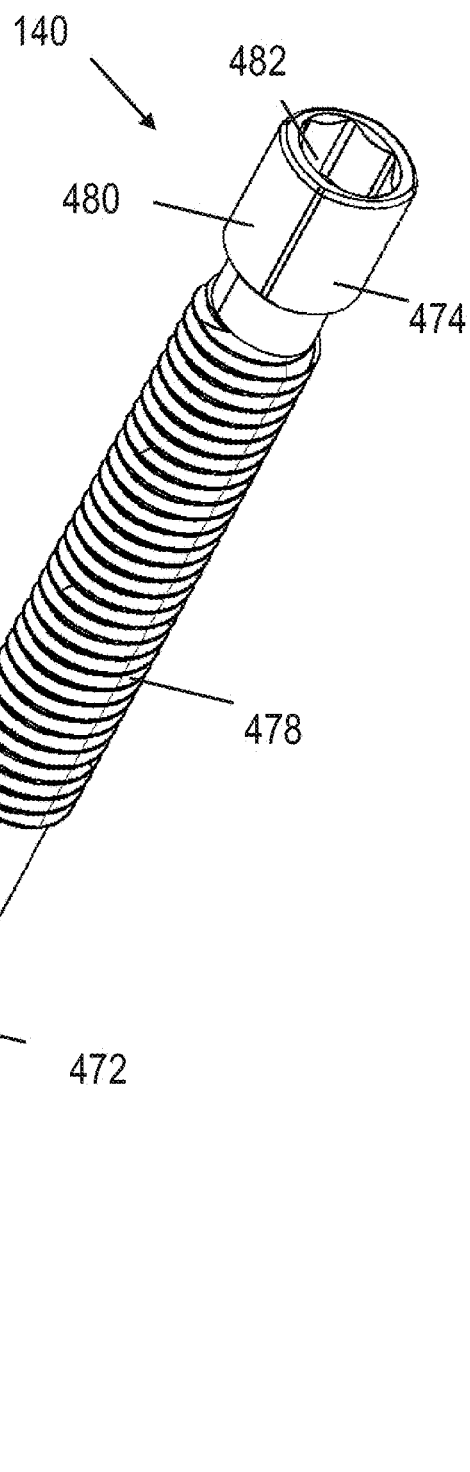
FIG. 4 is a diagram of a perspective view that illustrates a conventional vertical long rod pusher for use in the system.

Referring now to FIG. 2, the open extender 130 may include an upper body member 242A having a top end 244 and a lower body member 242B having a bottom end 246. The bottom end 246 may be tapered. The lower body member 242B may include a leg 248 having a first end integrated with and extending from the upper body member 242A. The upper body member 242A may include an elongated body section 253. An internal circumferential surface (not shown) of the body section 253 may include internal threads (not shown) for attachment of other surgical instruments, such as vertical rod pusher 140 (FIG. 4). The body section 253 will sometimes be referred to as a "modular instrument interface 253."

The open extender 130 may include a head cavity portion 230A formed in a free end of the leg 248 and configured to hold a head of fastener 160 (FIG. 1). The open extender 130 may include a locking collar 255 slidably coupled around the body section 253. The collar 255 may include diametrically opposing handles 264. Each handle 264 may have an actuator 266 which when pressed allows the collar 255 to slide up or down from unlocked (disengaged) to locked (engaged) positions. The actuators 266 may be spring biased.

The handle bar 112 may include a sleeve 212. The body section 253 of the open extender 130 may be configured slide within the sleeve 212 such that the elongated body section 253 may be concentric with the sleeve 212. Furthermore, the longitudinal axis of the handle bar 112 may be configured to align with a longitudinal axis of the sleeve 212. Hence, the modular instrument interface 253 may be configured to connect at least one additional instrument, such as lateral reducer 110. However, the modular instrument interface 253 may also connect the vertical rod pusher 140, for example, while the lateral reducer 110 is still connected to the open extender 130. Still further, the modular instrument interface 253 may connect other instruments while the lateral reducer 110 remains installed on the open extender 130.

Referring still to FIG. 2, the translating reducer arm 126 may include a head cavity portion 230B at a distal free end of the translating reducer arm 126. The translating reducer arm 126 may include a lateral side 223 and a medial side 225. The medial side 225 may include side rails 226 and an elongated cavity 228 between the side rails. The head cavity portion 230B may be formed in a free end of the elongated cavity 228. In the closed position, the elongated cavity 228 may be configured to encapsulate a portion of a vertical rod pusher 140 (FIG. 1, 6 or 7A-7C).

Figure 3:
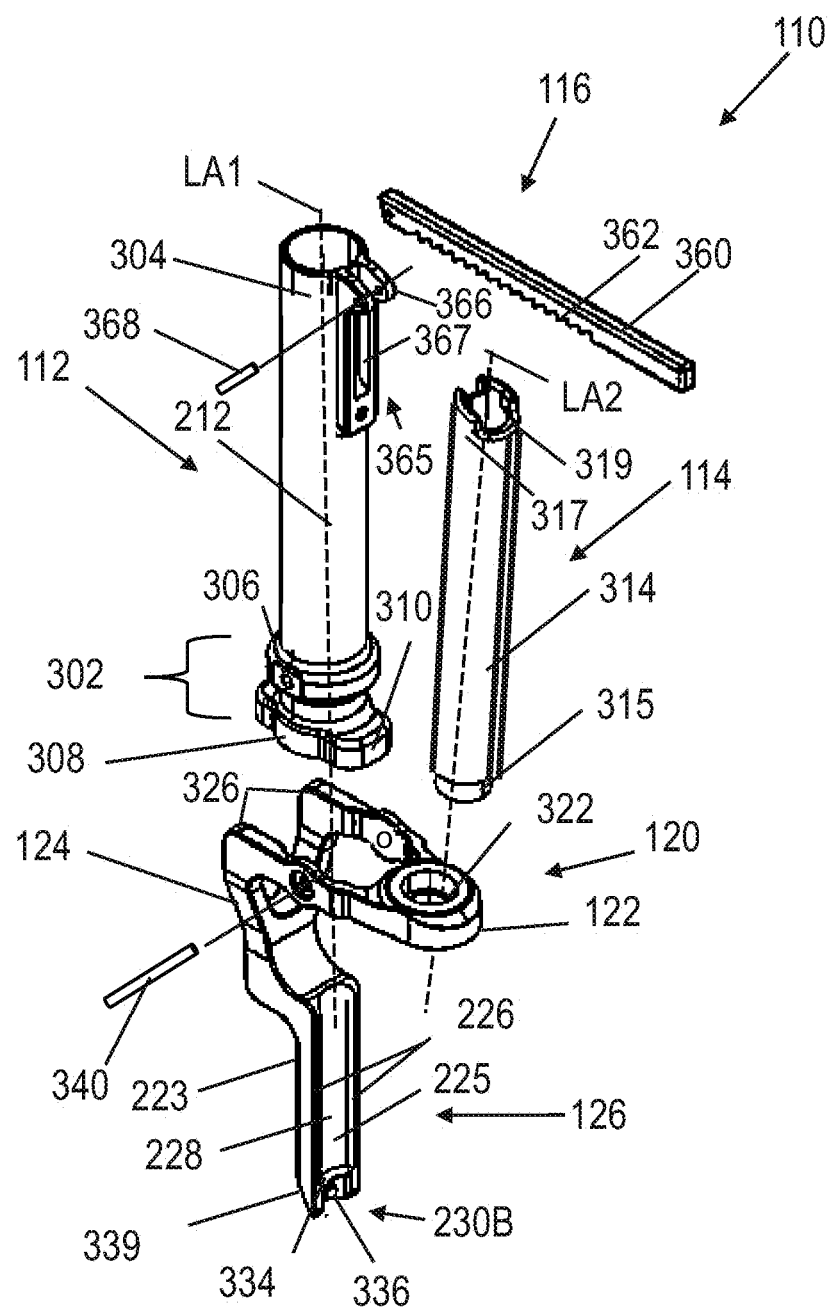
FIG. 3 is a diagram of an exploded view that illustrates components of a lateral reducer.

FIG. 3 is a diagram of an exploded view that illustrates components of a lateral reducer 110. The handle bar 112 may be referred to as a first handle bar 112. Handle bar 114 may be referred to as a second handle bar 114. The sleeve 212 of the handle bar 112 is an elongated handle structure having a first longitudinal axis LA1. A first end 302 of the sleeve 212 may be pivotally coupled to the first bracket member 122 via pivot pin 340 at the fulcrum 128 (FIGS. 1 and 2). A second end 304 of the sleeve 212 may be coupled to the ratchet assembly 116.

The second handle bar 114 may include an elongated handle structure such as sleeve 314. The sleeve 314 may have a second longitudinal axis LA2. The sleeve 314 may include a first end 315 and a second end 317. The second end 317 may be coupled to the ratchet assembly 116. The second end 317 may include diametrically opposing notches 319. The first end 315 may include a sleeve section with a circumference, which may be smaller than the circumference of sleeve 314.

The ratchet assembly 116 may include a ratchet arm 360 and a second fastener 365. The second fastener 365 may be a spring-biased pivot assembly. The second fastener 365 may include pivot arms 366 coupled to the first handle bar 112 and a pivot pin 368. The ratchet arm 360 may include ratchet teeth 362 and have one end pivotally coupled to the pivot arms 366 via the pivot pin 368. The second fastener 365 spring-biases, via spring 367, the ratchet arm 360 about the pivot arms 366. The teeth 362 of the ratchet arm 360 may engages diametrically opposing notches 319 in the second handle bar 114 and remain in place under the spring-bias force of spring 367.

In the embodiment of FIG. 1, the ratchet arm is slightly curved or arched. In the embodiment of FIG. 3, the ratchet arm 360 is essentially straight. Accordingly, the configuration of the ratchet arm may vary. While the handle bars are described as having sleeves, the sleeves may have indentions or a grip section for placement of fingers.

The first bracket member 122 may have a longitudinal axis angled relative to the first longitudinal axis LA1 and the second longitudinal axis LA2. The first bracket member 122 may include a seat 322 at one side and parallel arms 326 at the other side. The seat 322 may be dimension to receive the first end 315 of the second handle bar 114. Since the circumference of sleeve 314 is larger, than a circumference of the seat 322, the second handle bar 114 may be secured in the seat 322 via a compression force, as the sleeve 314 abuts a top rim of seat 322.

The first handle bar 112 may be a pivot bar. The second handle bar 114 may be a compression bar operable to apply a manual force of pressure (i.e., compression force) to maintain the first end 315 in the seat 322 and rotate the interface 120. The compression force may be created by moving the compression bar (i.e., second handle bar 114) along the ratchet arm 360 toward the pivot bar (i.e., first handle bar 112) by application of a manual force applied by a hand of a user. The ratchet arm 360 may apply an amount of compression force to the top of the sleeve 314 so that the second handle bar is held into position, even after the user's hand is removed.

The first end 302 of the sleeve 212 may include an interface connector 306 configured to be coupled at fulcrum 128 via a first fastener 340. The first end 302 may be include a collar interface 308. The interface connector 306 may be separated or distanced from the collar interface 308. The interface connector 306 may include a flange (denoted at 306) around the sleeve's circumference. The flange (denoted at 306) may include a hole that is configured to aligned with the fulcrum 128 and receive the pivot pin 340. The collar interface 308 may include a flange (denoted at 308) having first and second tabs 310 radially, extending from the flange (denoted at 308). The tabs 310 may be dimensioned to overlap with the handles 264 of collar 255 (FIG. 2).

The lateral side 223 of the translating reducer arm 126 may have a tapered end 339. In various embodiments, the tapered end 339 may approximate the profile of the tapered end of the extender 130. The head cavity portion 230B may be formed below the elongated cavity 228 and begins with upper rim 334. The head cavity portion 230B may include a projection 336 below the rim 334. The projection 336 may be configured to mate with an aperture in the head of a bone fastener or other connectors.

FIG. 4 is a diagram of a perspective view that illustrates a conventional vertical long rod pusher 140 for use in the system 100. The vertical long rod pusher 140 may include an elongated member 472 having a top end 474 and a bottom end 476 and a removable reducer pusher element 485. The elongated member 472 may include a threaded portion 478 at an upper end of the elongated member 472. The top end 474 may include a knob 480. The knob 480 may have an internal cavity that may be a tool fastener 482. In some embodiments, the tool fastener 482 may include a hexagonal coupler.

The elongated member 472 may include a circumference that fits within the upper body member 242A such that the threads on the inner circumferential wall (not shown) mate with threads of threaded portion 478. The reducer pusher element 485 may be affixed to the end of the elongated member 472 via upper collar 477, in some embodiments. The reducer pusher element 485 may have a rod seat 489. As the reducer pusher element 485 moves down, the rod seat 489 may apply a force to push the rod 103 (FIG. 1) into an implanted position.

In operation, the vertical long rod pusher 140 may be configured to turn in the upper body member 242A via a tool, such as driver 150, until the reducer pusher element 485 engages the rod 103, as shown in FIG. 7C.

Figure 5:
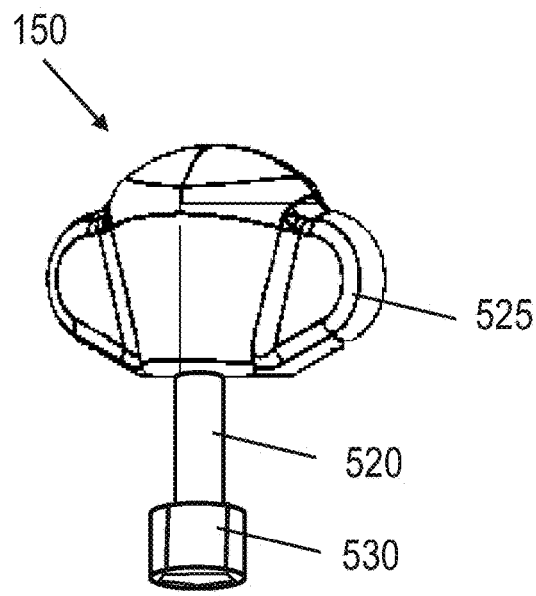
FIG. 5 is a diagram of a perspective view that illustrates a conventional driver for use in the system.

FIG. 5 is a diagram of a perspective view that illustrates a conventional driver 150 for use in the system 100. The driver 150 may include a driver shaft 520. The driver shaft 520 may have a handle 525 coupled to one end and a coupler 530 at a second end. The coupler 530 may be configured to be received in and mate with the tool fastener 482.

FIG. 6 is a sectional view below plane 6-6 of FIG. 1 that illustrates components of the modular surgical instrument system 100. In FIG. 6, a portion of the C-shape translation offset is shown. The C-shaped translation offset of the bracket may form a C-shaped profile so that the pivoting arm interface 120 curves around the collar 255 of extender 130 and loops back toward the open extender 130 and under the collar 255. In operation, the C-shaped translation offset may orient the translating reducer arm 126 essentially parallel to the leg 248 of the extender 130 when the translating reducer arm 126 is in a closed position. This allows the head cavity portion (i.e., head cavity portion 230B) to engage the head 669 of a bone fastener, for example.

The operation of the system 100 will now be described in relation to FIGS. 7A-7C. FIG. 7A is a partial side view that illustrates the modular surgical implant system 700A of FIG. 1 in a first (open) orientation. FIG. 7B is a partial side view that illustrates the modular surgical implant system 700B of FIG. 1 in an intermediate orientation. FIG. 7C is a partial side view that illustrates the modular surgical implant system 700C of FIG. 1 in a second (closed) orientation.

Those elements that are part of the system 700A, 700B, 700C will have a reference numeral that begins with "7". Those elements that are moving via the lateral reducer 710A in FIG. 7A end in an "A." Those elements that are moving via the lateral reducer 710B in FIG. 7B end in a "B." Those elements that are moving via the lateral reducer 710C in FIG. 7C end in a "C."

As shown in FIG. 7A, the lateral reducer 710A may sequentially drive the rod 703A inwards (meaning in the direction of the leg of the open extender 730) via side rails of the translating reducer arm 726A until the vertical rod pusher 740 can engage the rod 703A. The handle bars 712, 714A may have a first orientation, as best seen in FIG. 7A.

In FIG. 7A, the open extender 730 may have the fastener 760 held in the head cavity. The vertical rod pusher 740 may be coupled in the open extender 730. The pivoting arm interface 720A may be in a first seesaw position which orients the side with the second handle bar 714A at an elevation below the fulcrum 728. The other side of the interface 720A in the first seesaw position may be elevated above the fulcrum 728. The first orientation lifts the translating reducer arm 726A away from the open extender 730.

In FIG. 7B, the open extender 730 may have the fastener 760 held in the head cavity. The vertical rod pusher 740 may be coupled in the open extender 730. The second handle bar 714B may be moved closer to the first handle bar 712. The pivoting arm interface 720B may be in an intermediate seesaw position which orients the side with the second handle bar 714B at an intermediate elevation below the fulcrum 728. The other side of the interface 720A in the intermediate seesaw position may be elevated above the fulcrum 728. The intermediate seesaw position lifts the translating reducer arm 726A away from the open extender 730 but at a distance which is closer to the open extender 730. As the translating reducer arm 726A moves closer to the open extender 730, the translating reducer arm 726A may drive the rod 703B closer to the open extender 730 and the vertical rod pusher 740.

In FIG. 7C, the open extender 730 may have the fastener 760 held in the head cavity. The vertical rod pusher 740 may be coupled in the open extender 730. The second handle bar 714C may be moved still closer to the first handle bar 712. The pivoting arm interface 720C may be in a second seesaw position, which orients the side with the second handle bar 714B at an elevation that is essentially aligned with the fulcrum 728. The other side of the interface 720A in the second seesaw position may be aligned with the fulcrum 728. The second seesaw position lowers the translating reducer arm 726A so that the arm is essentially parallel with the leg of the open extender 730. As the translating reducer arm 726A moves closer to the open extender 730, the translating reducer arm 726A may drive the rod 703C closer to the open extender 730 and the vertical rod pusher 740. Once the rod 703C engage the vertical rod pusher 740, the rod pusher 740 pushes the rod downward in the direction of the fastener 760 until in place.

The second handle bar may be coupled to a second side of the interface and may have a first position, as shown in FIG. 7A, intermediate positions, as shown in FIG. 7B and a second position, as shown in FIG. 7C. The first position of the second handle bar 714A may orient the reducer arm 726A is in the open position. The second position of the second handle bar 714C may orient the reducer arm 726C is in the closed position. The intermediate positions of the second handle bar 714B between the first position and the second position may laterally rotates the reducer arm 726B to drives a surgical rod in a direction toward the second side of the interface 720B. Moreover, in some embodiments, the second position of the second handle bar 714C may orient the reducer arm 726C is in the closed position such that a longitudinal axis of rod 703C is essentially aligned orthogonal with the longitudinal axis of the first handle bar 712. In the closed position, the longitudinal axis of the reducer arm 726C is essentially parallel with the longitudinal axis of the first handle bar 712.

During spinal deformation or stabilization surgery, in situations where the rod rests medial or lateral to the top of the implant, it may be challenging to align the rod with the implant slot for the rod. In this case, a lateral reducer may be used to align the rod into the implant slot without the need for the surgeons to remove the open extender. The embodiments herein are also applicable to derotators. The lateral reducer may sequentially reduce the rod laterally to align with the head, for example of a bone fastener and hold the rod in the position. Thereafter, the vertical rod pusher may reduce the rod further into position in the head. The lateral reducer may remain coupled to the open extender and the vertical rod pusher. A derotator embodiment may use the handles of the lateral reducer themselves for derotation. The connection to the pedicle screw, for example, is very robust once the rod has been fully laterally reduced.

In some embodiments, the derotator may use a portion of the lateral reducer that slides over the proximal end of the open reducer, which could be shorter in length than the embodiment shown. This may allow existing derotation instruments to be used. In the latter configuration, the ratchet may be placed on the side or would have to pass through the handle attached to the pivoting arm.

The system may use multiple instruments that may be placed along an apex of curve. The reduction arm engages the contralateral rocker hole of the head, for example, once the reduction arm is fully laterally reduced to the closed position. This allows for additional leverage for vertical reduction. The lateral reducer may accommodate derotation instrumentation, as well. The derotation instrumentation may also be attached to the open extender with the lateral reducer. Other instruments that are intended to be used with the open extender may be used without interfering with the later reducer.

The system may be configured to allow the surgeon to derotate the appropriate levels of the spine without the extra step of removing the reducers.

Figure 8:
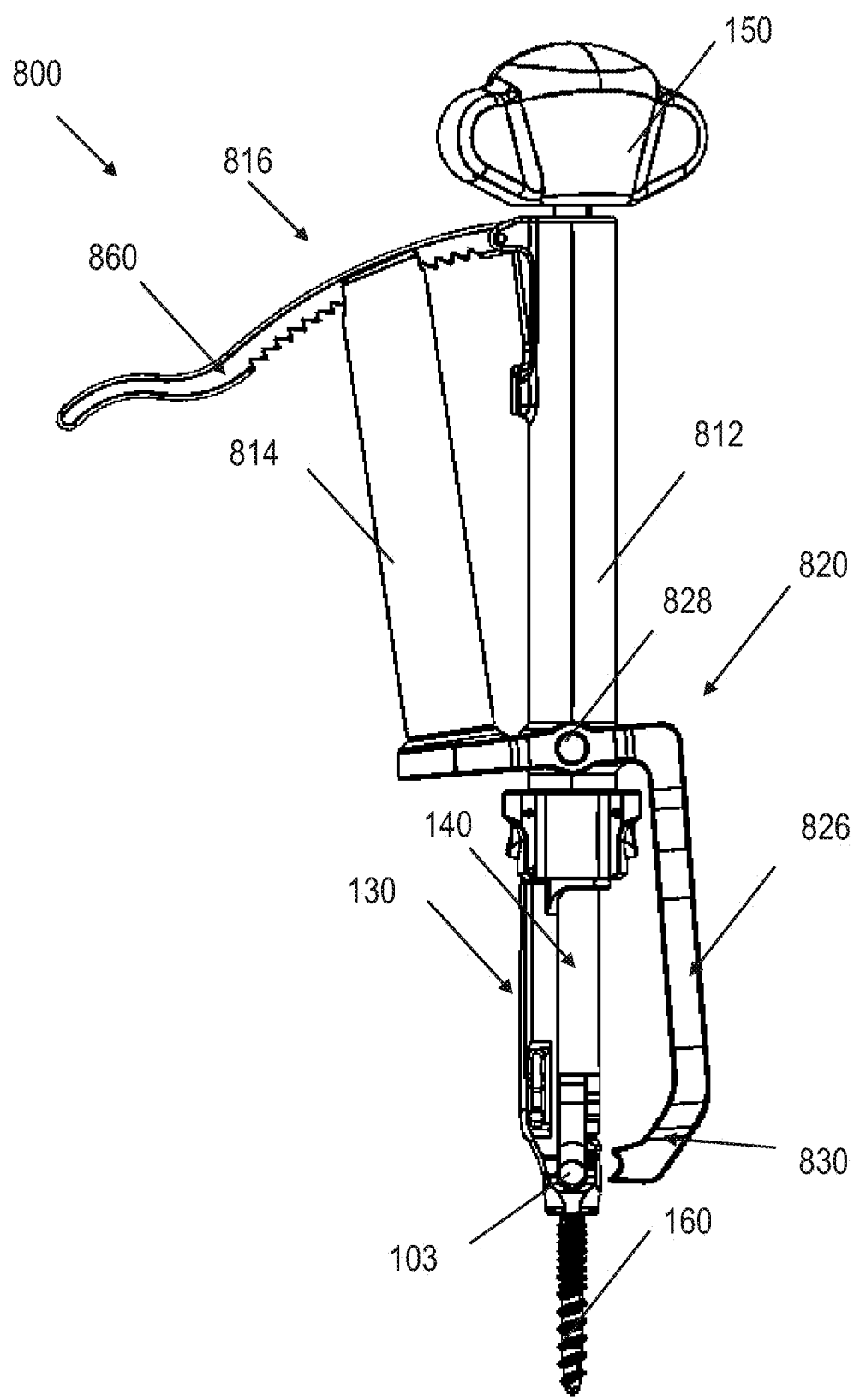
FIG. 8 is a diagram of another modular surgical implant system for the treatment of a patient's spine.
Figure 9:
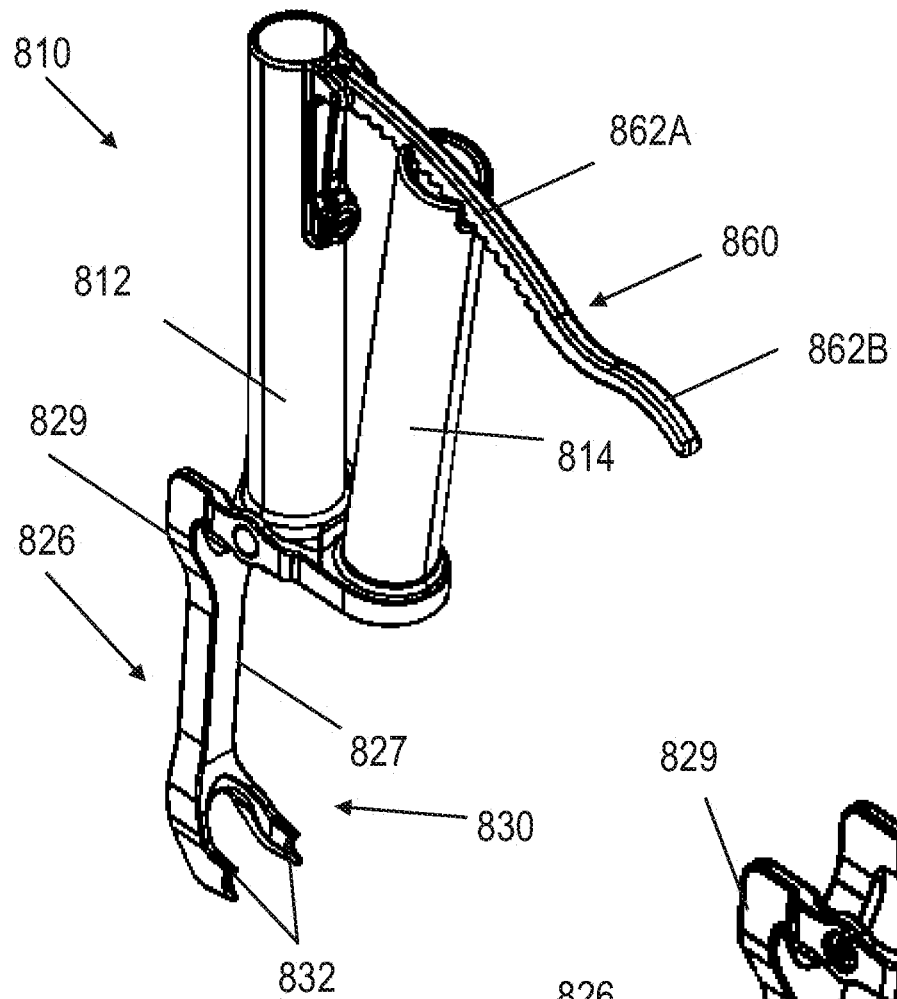
FIG. 9 is a diagram of a perspective view that illustrates a lateral reducer of the system in FIG. 8.
Figure 10:
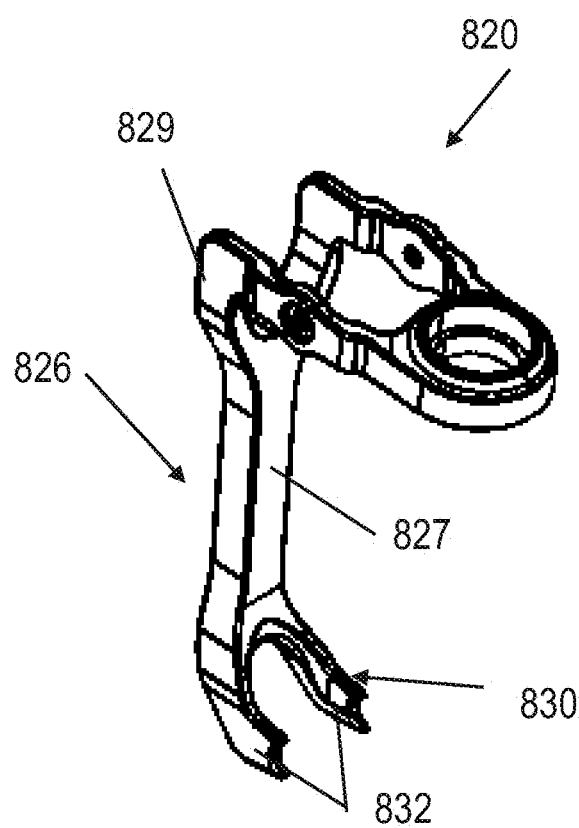
FIG. 10 is a diagram of a perspective view that illustrates an interface of the lateral reducer of FIG. 9.

FIG. 8 is a diagram of another modular surgical instrument system 800 for the treatment of a patient's spine. The system 800 also will be described in relation to FIGS. 9-10. Specifically, FIG. 9 is a diagram of a perspective view that illustrates a lateral reducer 810 of the system 800 in FIG. 8. FIG. 10 is a diagram of a perspective view that illustrates a pivoting arm interface 820 of the lateral reducer 810. The system 800 is essentially the same as the system 100. Thus, only the differences will be described in detail.

The lateral reducer 810 may include handle bars 812 and 814. The lateral reducer 810 may include a ratchet assembly 816 linking together the handle bars 812 and 814. The ratchet assembly 816 may include a ratchet arm 860 with a first section 862A and a second section 862B. The first section 862A may have a first curvature or arch shape. The second section 862B may include a second curvature. The second curvature may provide a designated lifting location to lift the free end of the ratchet arm 860. The ratchet arm 860 applies a compression force to hold the second handle bar 812 in a selected position.

The lateral reducer 810 may include a pivoting arm interface 820 having a fulcrum 828. A first side of the interface 820 may be integrated with the translating reducer arm 826. Unlike the embodiment of FIG. 1, the interface 820 does not include a bracket. The interface 820 may be a seesaw interface that may pivot about fulcrum 828. As the interface 820 pivots, the reducer arm 826 laterally rotates between an open position and a closed position. FIG. 8 illustrates an intermediate position of the reducer arm 826.

The lateral reducer 810 in FIG. 8 is shown installed on an open extender 130, previously described in FIGS. 1 and 2. The open extender 130 includes a head cavity portion, which holds a head of bone fasteners 160. The vertical long rod pusher 140 may be installed in the open extender 130 with the rod 103 pushed down into a head of a bone fastener 160. An example, vertical long rod pusher 140 is shown in FIG. 4.

In the embodiment of FIGS. 8-10, the translating reducer arm 826 includes an elongated member 827 having a first yoke end 829 and a second yoke end 830. The yoked end 829 is integrated or connected to the parallel arms (i.e., parallel arms 326) of the interface 820. The second yoke end 830 include parallel arms 832, which may extend in the direction of the open extender 830. More specifically, the parallel arms 832 are intended to receive the rod. In this case, the lateral reducer would be slide down to a height that allowed those forks to connect with the rod. Then, after lateral reduction, the lateral reducer would ride down the shaft of the extender during the vertical reduction. The longitudinal axis of the elongated member 827 may be configured to be parallel with an elongated axis of a leg of the open extender. The second yoke end 830 may include an indentation.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A lateral reducer comprising:
   a translating reducer arm including a first longitudinal axis and configured to laterally drive a rod;
   a pivoting arm interface having a fulcrum and a first side integrated with the translating reducer arm, the pivoting arm interface pivots the translating reducer arm about the fulcrum between an open position and a closed position;
   a first handle bar coupled to the pivoting arm interface at the fulcrum and having a second longitudinal axis; and
   a second handle bar coupled to a second side of the pivoting arm interface, the second handle bar movable between a first position, intermediate positions and a second position, where:
      in the first position, the translating reducer arm is in the open position,
      in the second position, the translating reducer arm is in the closed position such that the first longitudinal axis and the second longitudinal axis are parallel, and
      in intermediate positions between the first position and the second position, the translating reducer arm moves laterally in a direction toward the first handle bar.

2. The lateral reducer of claim 1, wherein the pivoting arm interface comprises:
   a first bracket member having a longitudinal axis intersecting the second longitudinal axis, the first bracket member being pivotally coupled to the first handle bar; and
   a second bracket member integrated with the first bracket member, the first and second bracket members form a C-shaped translation offset,
   wherein the translating reducer arm depends from a free end of the C-shaped translation offset.

3. The lateral reducer of claim 2, further comprising:
   a ratchet assembly with a ratchet arm;
   a first fastener; and
   a second fastener,
   wherein:
      the first handle bar includes:
         an elongated handle structure,
            a first end of the elongated handle structure pivotally coupled by the first fastener to the pivoting arm interface, and
            a second end of the elongated handle structure coupled to the ratchet arm by the second fastener; and the second handle bar includes:
   a first end coupled to the second side of the pivoting arm interface, and
   a second end coupled to a free end of the ratchet arm.

4. The lateral reducer of claim 3, wherein:
   the second fastener includes a spring-biased pivot assembly coupled to the second end of the first handle bar;
   the ratchet arm has one end coupled to the second fastener and extends radially from the first handle bar;
   the ratchet arm includes ratchet teeth configured to be coupled to notches in the second end of the second handle bar; and
   the spring-biased pivot assembly spring biases the ratchet teeth in the notches of the second handle bar to maintain the second handle bar in a selected one of the first position, the second position and any intermediate position.

5. The lateral reducer of claim 4, wherein:
   the second handle bar is coupled to the second side of the pivoting arm interface and configured to receive a manual force of pressure to cause the pivoting arm interface to pivot about the fulcrum connected to the first handle bar.

6. The lateral reducer of claim 1, wherein the translating reducer arm comprises:
   a lateral side;
   a medial side;
   side rails on the medial side;
   an elongated cavity between the side rails; and
   a head cavity portion formed in a free end of the elongated cavity, the head cavity portion configured to connect to a contralateral rocker hole of a head of a bone fastener.

7. The lateral reducer of claim 1, wherein the translating reducer arm comprises:
   a first yoke end integrated with the pivoting arm interface;
   a second yoke end; and
   an elongated member between the first yoke end and the second yoke end.

8. The lateral reducer of claim 7, wherein the second yoke end includes an indentation to connect to a contralateral rocker hole of a head of a bone fastener.

9. A modular surgical instrument, comprising:
   an extender comprising a modular instrument interface, an extender leg having a first longitudinal axis and a head cavity portion at an end of the extender leg; and
   a lateral reducer comprising:
      a translating reducer arm including a second longitudinal axis, the translating reducer arm having an open position orienting the second longitudinal axis angled relative to the first longitudinal axis and a closed position orienting the second longitudinal axis aligned with the first longitudinal axis,
      a first handle bar coupled to the modular instrument interface,
      a second handle bar coupled to the translating reducer arm, the second handle bar sequentially pivots the translating reducer arm laterally toward the extender leg to the closed position, and
      a ratchet assembly linking the first handle bar and the second handle bar.

10. The modular surgical instrument of claim 9, wherein:
    the extender comprises a locking collar;
    the lateral reducer further comprises a bracket having a first side integrated with the translating reducer arm and coupled to the first and second handle bars; and the bracket comprising:
a first bracket member having a longitudinal axis angled relative to the second longitudinal axis, the first bracket member intersecting with and coupled to the first handle bar at a fulcrum and the second handle bar at a second side of the bracket opposite the first side, and
a second bracket member integrated with a first side of the first bracket member, the first and second bracket members form a C-shaped translation offset to extend around the locking collar,
wherein the translating reducer arm depends from a free end of the C-shaped translation offset.

11. The modular surgical instrument of claim 10, further comprising:
a first fastener; and
a second fastener,
wherein:
the ratchet assembly includes a ratchet arm;
the first handle bar includes:
an elongated handle structure,
a first end of the elongated handle structure pivotally coupled by the first fastener to the first bracket member, and
a second end of the elongated handle structure coupled to the ratchet arm by the second fastener; and
the second handle bar includes:
a first end coupled to the first bracket member, and
a second end coupled to a free end of the ratchet arm.

12. The modular surgical instrument of claim 11, wherein:
the second handle bar is coupled, by a compression force exerted by the ratchet arm, to the second side of the bracket and configured to apply a manual force of pressure to pivot the first bracket member about the fulcrum connected to the first handle bar.

13. The modular surgical instrument of claim 9, wherein the translating reducer arm comprises:
a lateral side;
a medial side;
side rails on the medial side;
an elongated cavity between the side rails; and
a head cavity portion formed in a free end of the elongated cavity, the head cavity portion configured to connect to a contralateral rocker hole of a head of a bone fastener.

14. The modular surgical instrument of claim 9, wherein the translating reducer arm comprises:
a first yoke end;
a second yoke end; and
an elongated member between the first yoke end and the second yoke end.

15. A method, comprising:
providing a modular surgical instrument comprising:
an extender comprising a modular instrument interface, an extender leg having a first longitudinal axis and a head cavity portion at an end of the extender leg; and
a lateral reducer comprising:
a translating reducer arm including a second longitudinal axis, the translating reducer arm having an open position orienting the second longitudinal axis angled relative to the first longitudinal axis and a closed position orienting the second longitudinal axis aligned with the first longitudinal axis,
a first handle bar coupled to the modular instrument interface, and
a second handle bar coupled to the translating reducer arm, the second handle bar sequentially pivots the translating reducer arm laterally toward the extender leg to the closed position;
coupling the first handle bar of the lateral reducer to the modular instrument interface of the extender;
by the lateral reducer, sequentially reducing laterally a rod toward the extender leg; and
prior to laterally reducing the rod, locking a head of a bone fastener in the extender.

16. The method of claim 15, further comprising:
providing a vertical rod pusher;
installing the vertical rod pusher in the modular instrument interface, while the lateral reducer remains coupled to the modular instrument interface; and
after laterally reducing the rod, vertically reducing the rod.

17. The method of claim 16, further comprising:
encapsulating a portion of the vertical rod pusher by the translating reducer arm, after laterally reducing the rod, wherein the translating reducer arm has a profile that resembles a profile of the extender leg.

18. The method of claim 16, further comprising:
engaging the translating reducer arm with a contralateral rocker hole of the head of the bone fastener, after laterally reducing the rod.

19. The method of claim 15, wherein the sequentially reducing the rod includes:
ratcheting, by the ratchet assembly, the second handle bar of the lateral reducer toward the first handle bar;
while ratcheting the second handle bar, applying a compression force to pivot the translating reducer arm; and
holding a position of the second handle bar and the translating reducer arm by the ratchet assembly.

20. The method of claim 19, wherein:
the lateral reducer includes a seesaw interface coupled the translating reducer arm, the first handle bar and the second handle bar; and
the applying of the compression force includes:
applying the compression force to one side of the seesaw interface by the second handle bar; and
further comprising:
pivoting the seesaw interface about the first handle bar.

* * * * *